United States Patent [19]

Bortolo et al.

[11] Patent Number: 5,397,570

[45] Date of Patent: * Mar. 14, 1995

[54] ANTIBIOTICS AB-023 AND PROCESS FOR PREPARING THEM

[75] Inventors: Rossella Bortolo; Dante Cidaria, both of Novara; Giorgio Cassani, Arluno; Adriana Vallesi, Castelraimondo; Gianfranco Gugliemetti, Bogogno; Giorgio Borgonovi, Milan; Silvia Spera, Novara; Giorgio Pirali, Seronno; Giovanni Confalonieri, Monza, all of Italy

[73] Assignee: Ministero Dell 'Universita' E Della Ricerca Scientifica E Tecnologica, Rome, Italy

[ * ] Notice: The portion of the term of this patent subsequent to Jan. 18, 2011 has been disclaimed.

[21] Appl. No.: 136,754

[22] Filed: Oct. 15, 1993

Related U.S. Application Data

[62] Division of Ser. No. 747,018, Aug. 19, 1991, Pat. No. 5,279,829.

[30] Foreign Application Priority Data

Aug. 21, 1990 [IT] Italy ..................... 21293/90

[51] Int. Cl.$^6$ ...................... A61K 35/74; A61K 35/66
[52] U.S. Cl. ..................................... 424/122
[58] Field of Search ......................... 424/122

*Primary Examiner*—Jerome D. Goldberg
*Attorney, Agent, or Firm*—Oblon, Spivak, McClelland, Maier & Neustadt

[57] ABSTRACT

The Antibiotic Complex AB-023 and its components: Antibiotic AB-023a and Antibiotic AB-023b are disclosed, which are obtained by the controlled aerobic culture of *Streptomyces sp.* NCIMB 40212 in an aqueous nutrient culture substrate. Antibiotics AB-023 display a biological activity against pathogen fungi which attack agricultural crops and man.

1 Claim, 12 Drawing Sheets

ANTIBIOTICS AB-023 AND PROCESS FOR PREPARING THEM

This application is a division of U.S. application Ser. No. 07/747,018, filed Aug. 19, 1991, now U.S. Pat. No. 5,279,829.

The present invention relates to antibiotic substances designated as <<Antibiotic Complex AB-023>> and to its components: Antibiotic AB-023a and Antibiotic AB-023b.

The present invention relates furthermore to the process for preparing said Antibiotics AB-023, by means of the fermentation of *Streptomyces sp.* NCIMB 40212, and to their use in the treatment of phytopathologies caused by the fungal species sensible to said antibiotics.

The <<Antibiotic Complex AB-023>> and its components: Antibiotic AB-023a and Antibiotic AB-023b are different from the other antibiotics known from the prior art.

By the term <<Antibiotic Complex AB-023>>, as used in the instant disclosure, a mixture is meant which comprises all those components, endowed with one or more biological activities, which are produced by the fermentation of *Streptomyces sp.* NCIMB 40212 under such conditions as specified in detail in the following.

Said biologically active components comprise, but are not limited to, those designated as <<Antibiotic AB-023a>> and <<Antibiotic AB-023b>>, isolated from the mixture.

As those skilled in the art of fermentations are well aware of, the number and the relative ratio of the components which constitute the Antibiotic Complex AB-023 may vary, depending on the fermentation conditions (such as, e.g., the culture substrate, the fermentation temperature, the duration of the same fermentation, the aeration, and so forth), and of the bacterial strain used.

One should furthermore understand that the scope of the instant invention is not limited to the use of *Streptomyces sp.* NCIMB 40212, but that it also encompasses the use of variants and/or mutants obtained either naturally or artificially from said microorganism, provided that they are capable of producing the Antibiotics AB-023.

Therefore, an object of the instant invention is the Antibiotic Complex AB-023 which can be obtained by cultivating under controlled, aerobic, conditions, *Streptomyces sp.* NCIMB 40212, or an equivalent thereof which is a natural or artificial variant or mutant thereof, in an aqueous nutrient culture substrate, containing assimilable carbon and nitrogen sources, inorganic salts and metal in trace amounts, and subsequently separating said Antibiotic Complex AB-023 and its Antibiotic AB-023a and Antibiotic AB-023b components.

Physical-Chemical Characteristics of Antibiotic Complex AB-023

Figure 1:
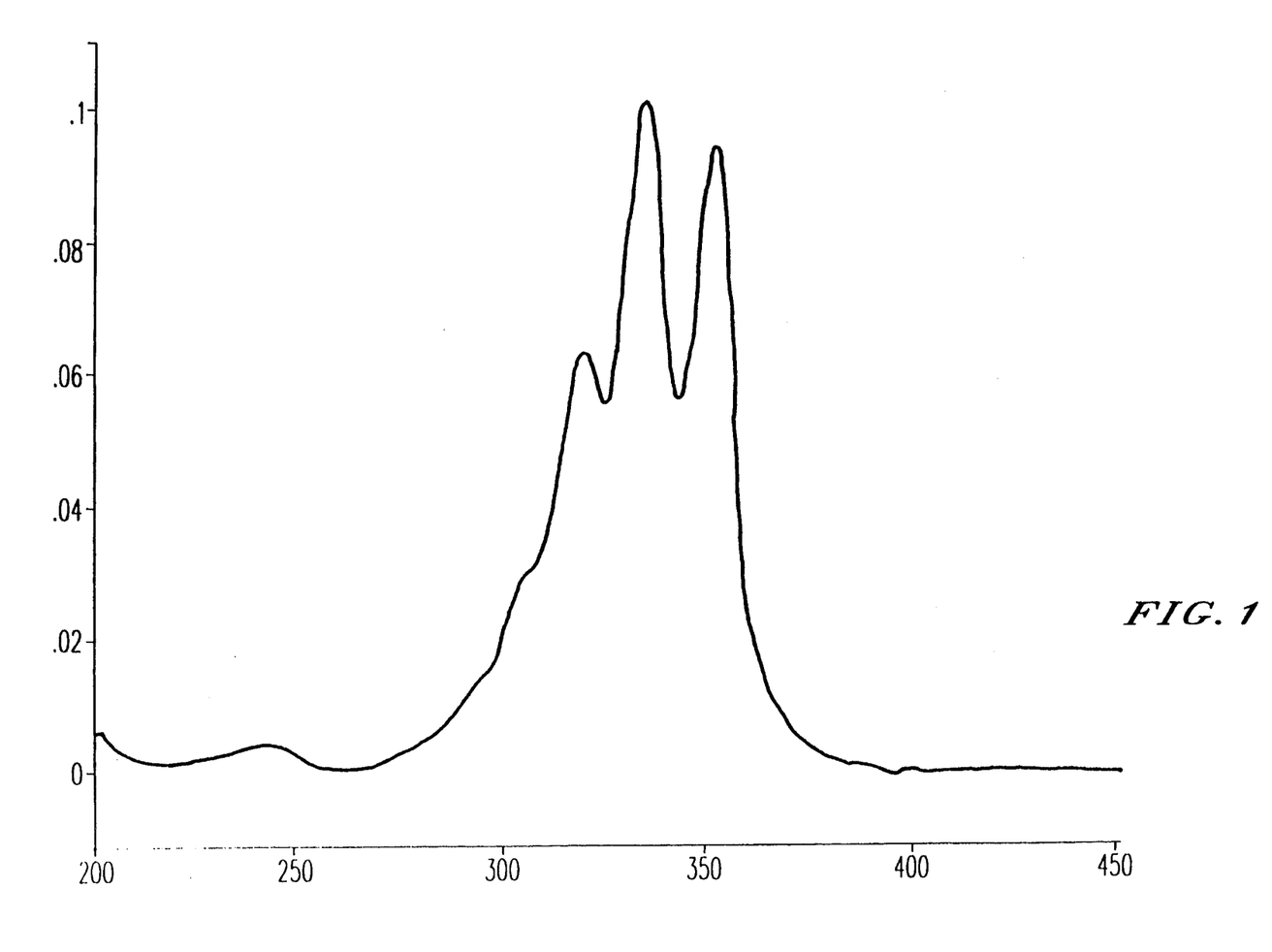
Figure 2:
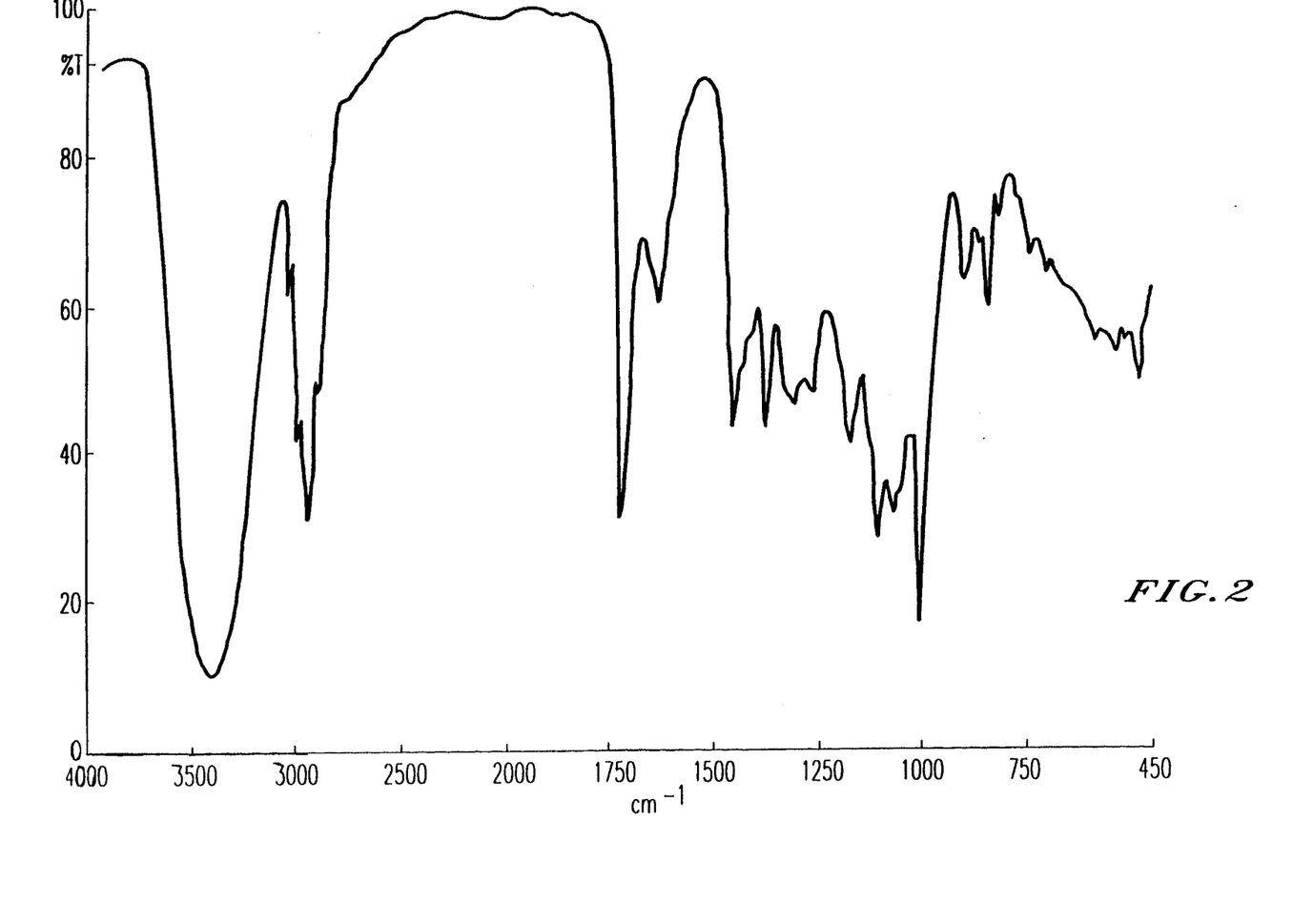
Figure 3:
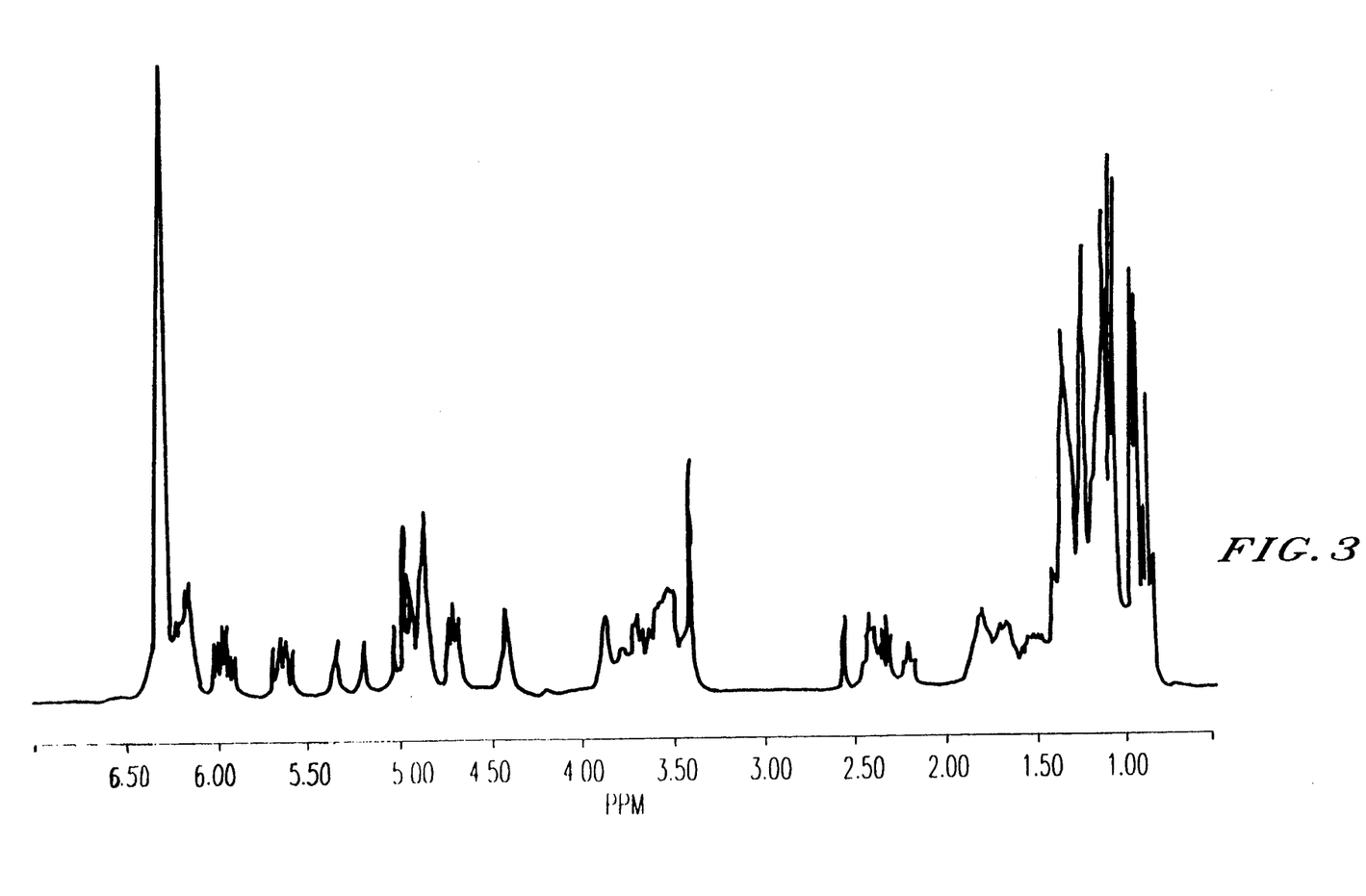

The Antibiotic Complex AB-023 is mainly constituted by Antibiotic AB-023a and Antibiotic AB-023b, and has the appearance of a yellow powder, characterized by:

(a) good solubility in dimethyl-sulfoxide, methanol, ethanol, methanol:water (1:1, volume/volume [v/v]) mixture and ethanol:water (1:1, v/v) mixture, insolubility in water, hydrocarbons, acetonitrile, methylene chloride, chloroform;

(b) approximate elemental analysis, as determined on a sample kept under vacuum at 40° C. for two hours, as percent values: carbon: 64.06; hydrogen: 8.78; the product does not contain nitrogen, phosphorus and sulfur;

(c) the ultra-violet (U.V.) absorption spectrum is reported in FIG. 1 ot the accompanying drawings; it shows absorbance peaks at 304.0 nm, 317.2 nm, 332.4 nm, 350.4 nm at a concentration of 0.022 mg/ml in ethanol:water (50:50 v/v);

(d) the infrared (I.R.) absorption spectrum in KBr tablet is reported in FIG. 2 of the accompanying drawings, and shows the following absorption peaks ($cm^{-1}$): 3402, 3014, 2970, 2936, 2879, 2041, 1725, 1636, 1457, 1379, 1311, 1266, 1175, 1109, 1072, 1008, 905, 847, 823, 745, 706, 583, 535, 515, 480;

(e) the N.M.R. spectrum of $^1H$ is reported in FIG. 3, and shows signals recorded with a Bruker Spectrometer AM at 300 MHz in hexadeutero-dimethylsulfoxide (DMSOd6); the chemical shifts were indirectly referred to TMS=0.00 ppm (TMS) by using as the internal reference the central peak of hexadeutero-dimethylsulfoxide taken at TMS=2.56 ppm.

(ppm): 6.43–6.24 (m, 12H); 6.24–6.07 (m, 4H); 5.96 (m, 2H); 5.62 (m, 2H); 5.33 (bs, 1H); 5.19 (bs, 1H); 5.03 (bs, 1H); 4.96 (bs, 2H); 4.93 (bs, 1H); 4.86 (m, 4H); 4.70 (m, 2H); 4.42 (bs, 2H); 3.94–3.36 (m, 12H); 2.41 (m, 2H); 2.32 (m, 1H); 2.20 (m, 1H); 1.92–1.45 (m, 6H); 1.45–1.09 (m, 42H); 1.25 (d, 6H); 1.11 (d, 3H); 1.07 (d, 6H); 0.95 (d, 6H); 0.88 (t, 3H).

Figure 4:
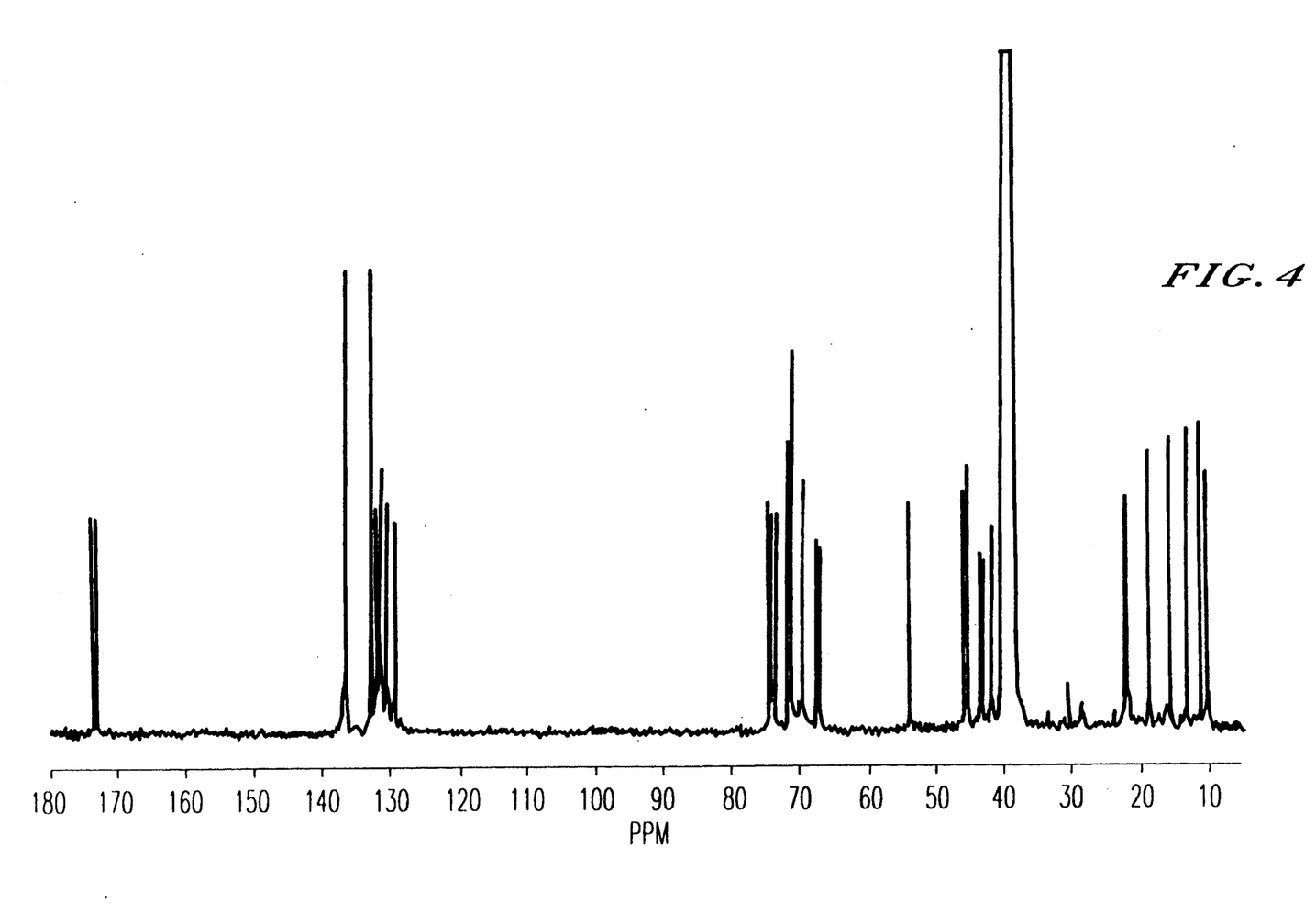

(f) the N.M.R. spectrum of $^{13}C$ is reported in FIG. 4 and shows signals recorded with a Bruker Spectrometer AM at 300 MHz in hexadeutero-dimethylsulfoxide (DMSOd6); the chemical shifts were indirectly referred to TMS=0.00 ppm (TMS) by using as the internal reference the central peak of hexadeutero-dimethylsulfoxide taken at TMS=39.50 ppm.

The data relevant to the multiplicity of the signals were obtained by means of DEPT experimental tests at 45°, 90°, and 135°;

(ppm): 173.7 (s); 173.1 (s); 136.5 (d); 136.5 (d); 136.5 (d); 136.3 (d); 133.1 (d); 133.1 (d); 132.9 (d); 132.9 (d); 132.7 (d); 132.5 (d); 132.1 (d); 131.9 (d); 131.6 (d); 131.4 (d); 131.2 (d); 131.1 (d); 130.6 (d); 130.3 (d); 129.5 (d); 129.2 (d); 74.7 (d); 74.4 (d); 74.1 (d); 73.6 (d); 72.0 (d); 71.9 (d); 71.5 (d); 71.4 (d); 71.4 (d); 71.2 (d); 69.7 (d); 69.6 (d); 67.7 (d); 67.3 (d); 54.1 (d); 46.1 (d); 45.5 (d); 45.4 (d); 43.4 (t); 42.9 (t); 41.7 (t); 41.5 (t); 40.1 (d); 39.5 (d); 38.9 (t); 38.9 (t); 38.8 (t); 38.7 (t); 38.2 (t); 38.1 (t); 22.5 (t); 22.4 (t); 22.1 (t); 19.0 (q); 18.7 (q); 15.9 (q); 15.6 (q); 13.2 (q); 11.3 (q); 10.4 (q); 10.2 (q).

(g) the retention time ($R_t$) of Antibiotic Complex AB-023, identified as one single peak, is of approximately 3.65 minutes when analysed by HPLC on a reverse-phase column under the following conditions:

* column: Merck's Lichrosorb RP-18, mm 250×4
* precolumn: Merck C18
* eluent: MeOH:$H_2O$ (66:14 v/v)
* flowrate: 1 ml/minute
* detector: U.V., 333 nm
* temperature: 35° C.

The retention times of the individual antibiotic components: AB-023a and AB-023b, as resolved peaks, is of 6.18 minutes and 6.76 minutes, respectively, when analysed by HPLC on a reverse-phase column under the following conditions:

* column: Merck's Lichrosorb RP-18, mm 250×4
* precolumn: Merck C18

* eluent: acetonitrile:H₂O (52:48 v/v)
* flowrate: 1 ml/minute
* detector: U.V., 333 nm
* temperature: 35° C.

Physical-Chemical Characteristics of Antibiotic AB-023a

The Antibiotic AB-023a has the appearance of a yellow powder, characterized by:

(a) good solubility in dimethyl-sulfoxide, methanol, ethanol, methanol:water (1:1, v/v) mixture and ethanol:water (1:1, v/v) mixture, insolubility in water, hydrocarbons, acetonitrile, methylene chloride, chloroform;

(b) approximate elemental analysis, as determined on a sample kept under vacuum at 40° C. for two hours, as percent values: carbon: 63.88; hydrogen: 8.64; the product does not contain nitrogen, phosphorus and sulfur;

(c) the molecular weight of Antibiotic AB-023a is of 550 Da, as it can be inferred from its FAB-MS spectrum, showing a peak at m/z=551 Da, corresponding to [MH]⁺ ion, and a peak at m/z=549 Da, corresponding to [M−H]⁻ ion. The operating conditions are as follows: FAB negative ions and positive ions, Xe at 9.5 kV, matrix glycerol, Finning Mat 8424;

(d) the most probable minimal formula of Antibiotic AB-023a results to be: $C_{31}H_{50}O_8$ as deduced from the data from ¹H-N.M.R. and ¹³C-N.M.R. spectroscopy and from mass spectrometry.

Figure 5:
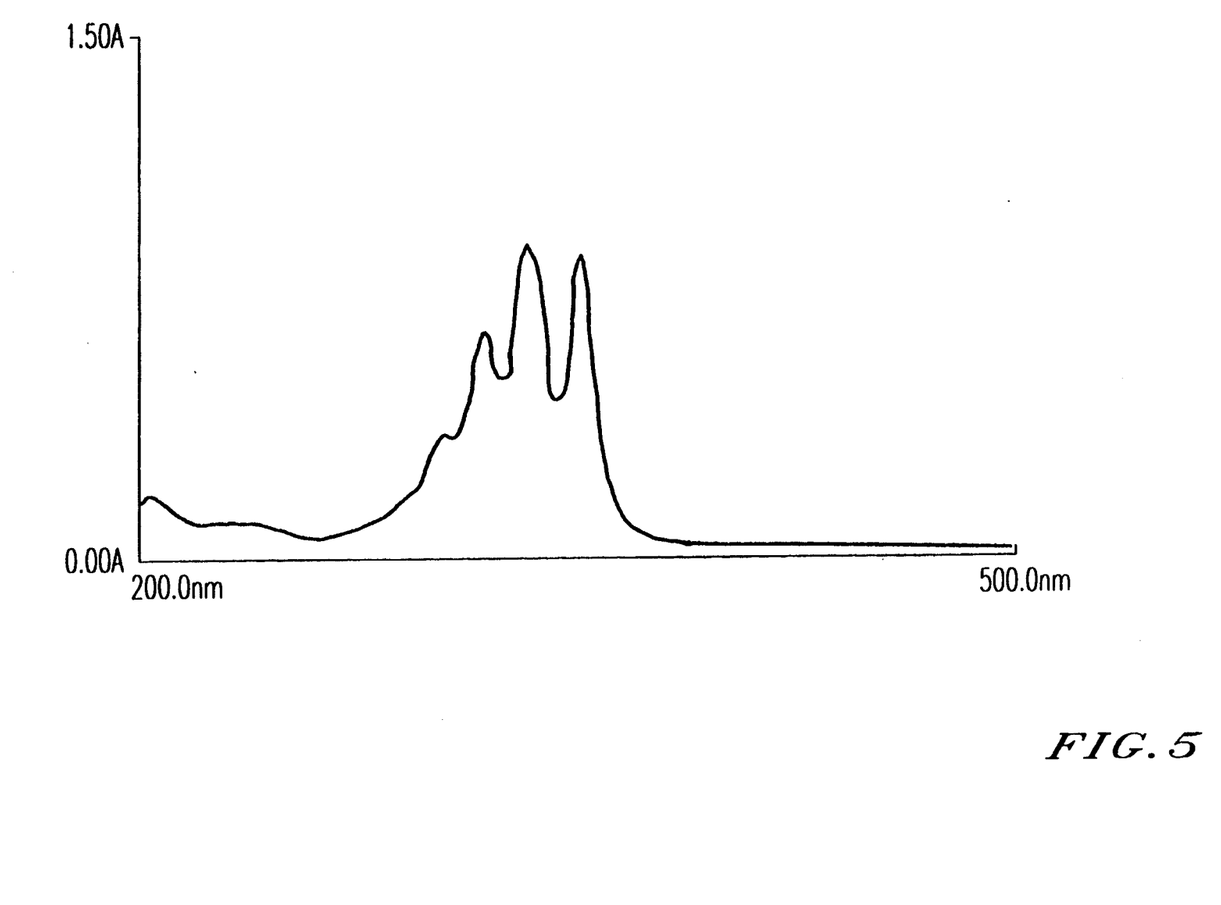
Figure 6:
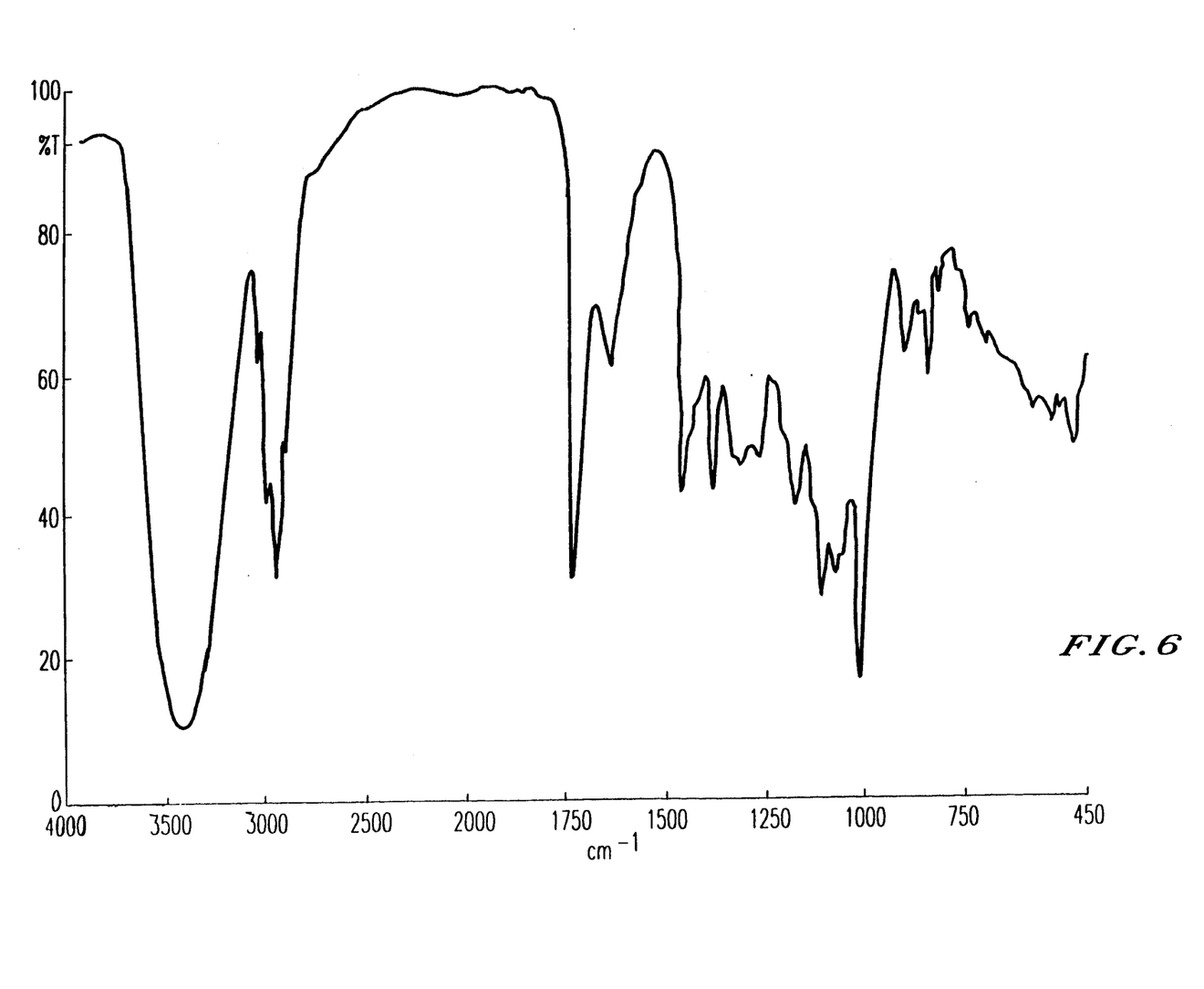
Figure 7:
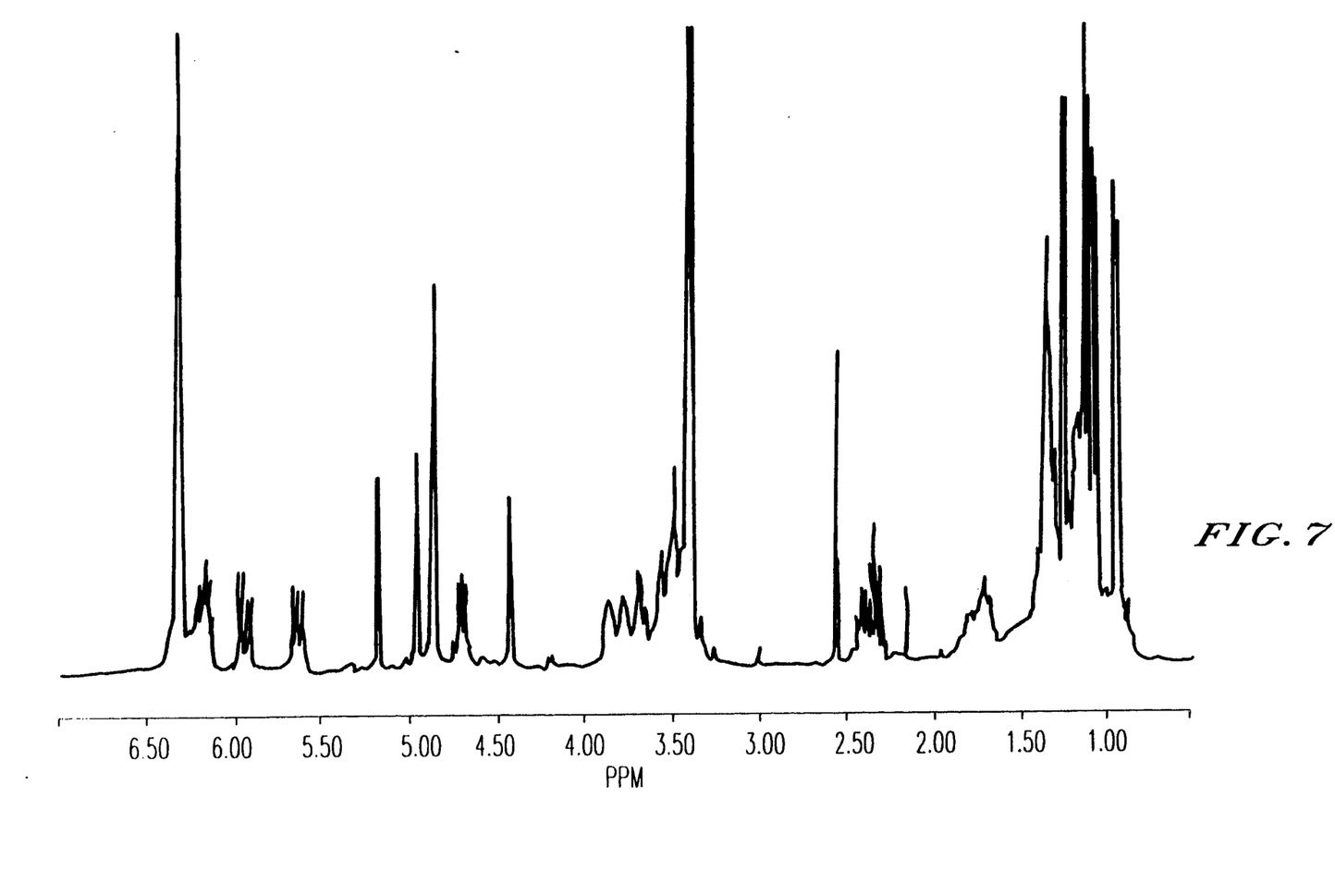

(e) the ultra-violet (U.V.) absorption spectrum is reported in FIG. 5 of the accompanying drawings; it shows absorbance peaks at 303.0 nm (=22678), 316.6 nm (=44979), 331.6 nm (=71198), 349.8 nm (=71952), at a concentration of 0.073 mg/ml in ethanol;

(f) the infrared (I.R.) absorption spectrum in KBr tablet is reported in FIG. 6 of the accompanying drawings, and shows the following absorption peaks (cm⁻¹): 3402, 3014, 2970, 2936, 2879, 2041, 1725, 1636, 1457, 1379, 1311, 1266, 1175, 1109, 1072, 1008, 905, 847, 823, 745, 706, 583, 535, 515, 480;

(e) the N.M.R. spectrum of ¹H is reported in FIG. 7, and shows signals recorded with a Bruker Spectrometer AM at 300 MHz in hexadeutero-dimethylsulfoxide (DMSOd6); the chemical shifts were indirectly referred to TMS=0.00 ppm (TMS) by using as the internal reference the central peak of hexadeuterodimethylsulfoxide taken at TMS=2.56 ppm (the more largely overlapped signals were identified by means of bidimensional-N.M.R. techniques);

(ppm): 6.32 (m, 6H); 6.17 (m, 1H); 6.16 (m, 1H); 5.93 (dd, 1H); 5.64 (dd, 1H); 5.18 (d, 1H); 4.96 (d, 1H); 4.87–4.85 (m, 3H); 4.70 (m, 1H); 4.43 (d, 1H); 3.86 (m, 1H); 3.77 (m, 1H); 3.68 (m, 1H); 3.57 (m, 1H); 3.51 (m, 1H); 3.48 (m, 1H); 2.40 (m, 1H); 2.32 (m, 1H); 1.68 (m, 1H); 1.46–1.09 (m, 14H); 1.24 (d, 3H); 1.11 (d, 3H); 1.07 (d, 3H); 0.93 (d, 3H).

Figure 8:
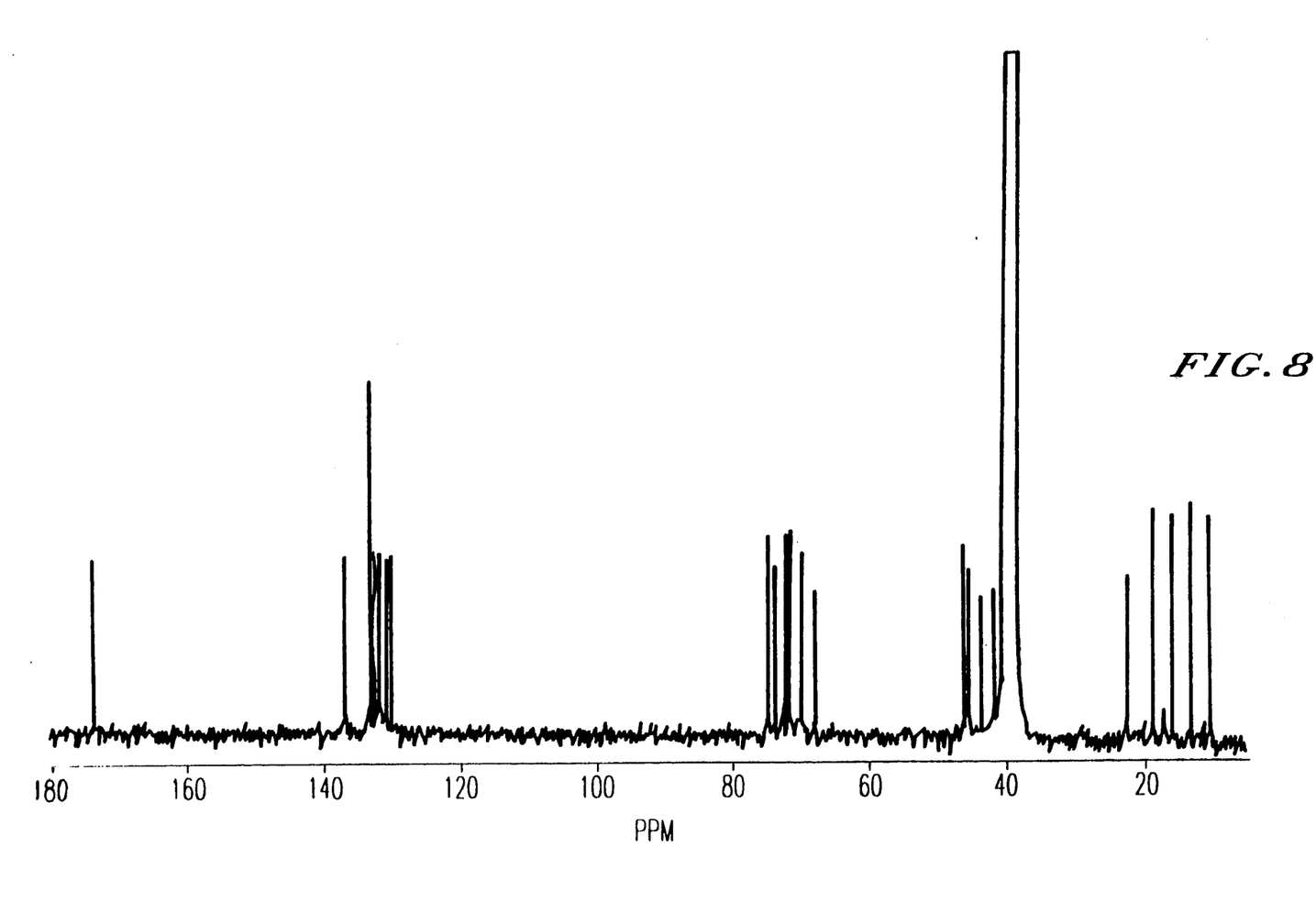
Figure 9:
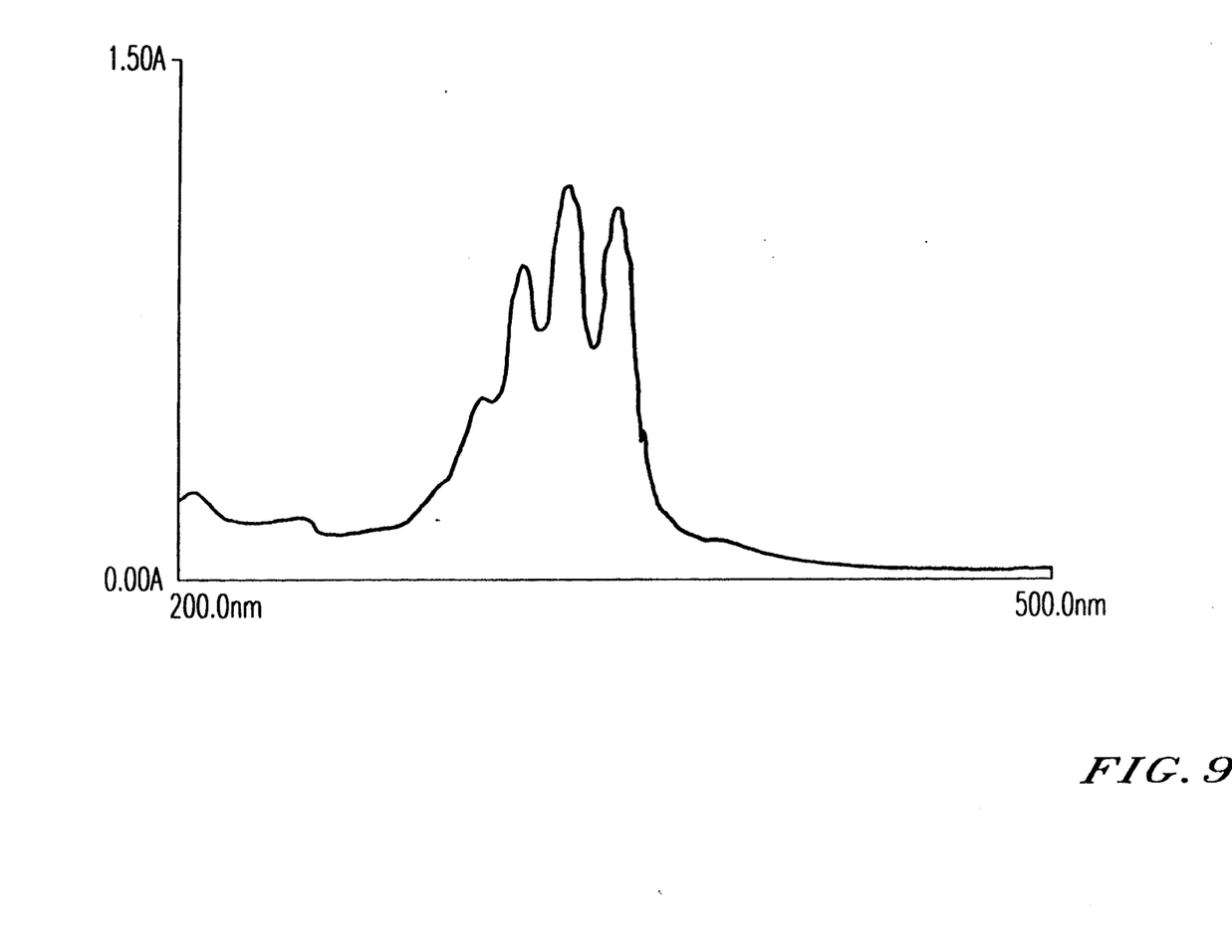

(h) the N.M.R. spectrum of ¹³C is reported in FIG. 8 and shows signals recorded with a Bruker Spectrometer AM at 300 MHz in hexadeutero-dimethylsulfoxide (DMSOd6); the chemical shifts were indirectly referred to TMS=0.00 ppm (TMS) by using as the internal reference the central peak of hexadeuterodimethylsulfoxide taken at TMS=39.50 ppm.

The data relevant to the multiplicity of the signals were obtained by means of DEPT experimental tests at 45°, 90°, and 135°;

(ppm): 173.7 (s); 136.5 (d); 136.3 (d); 132.9 (d); 132.9 (d); 132.5 (d); 132.1 (d); 131.6 (d); 131.2 (d); 130.3 (d); 129.5 (d); 74.4 (d); 73.6 (d); 72.0 (d); 71.4 (d); 71.2 (d); 69.6 (d); 67.7 (d); 46.1 (d); 45.4 (d); 43.4 (t); 41.5 (t); DMSO*; DMSO*; DMSO*; 38.2 (t); 22.4 (t); 18.7 (q); 15.9 (q); 13.2 (q); 10.4 (q);

(*): these peaks are covered by the strong signal generated by the solvent;

(i) the retention coefficients in thin-layer chromatography with an eluent run of 15 cm on reverse-phase silica slabs RP-18 F 254 (Merck-Schuchardt) and on reverse-phase silica slabs RP-8 F 254 (Merck-Schuchardt), in the following eluent systems are:

* A eluent=water
* B eluent=acetonitrile
* C eluent=methanol
* D eluent=10 mM solution of $KH_2PO_4$ in $H_2O$ adjusted at pH=3 with $H_3PO_4$;

|  | A:B 50:50 (v/v) eluent system | | C:D 70:30 (v/v) eluent system | |
| --- | --- | --- | --- | --- |
| AB-023a | RP-8 | RP-18 | RP-8 | RP-18 |
|  | 0,30 | 0,16 | 0,14 | 0.00 |

Visualization:
(1) fluorescence under UV-light (355 nm)
(2) reactant prepared by dissolving 20 g of $(NH_4)_3MoO_4$ and 1 g of $Ce(SO_4)_2$ in an aqueous solution containing 6% of $H_2SO_4$;

(1) the retention time of Antibiotic AB-023a is of approximately 6.18 minutes when analysed by HPLC on a reverse-phase column under the following conditions:

* column: Merck's Lichrosorb RP-18, mm 250×4
* precolumn: Merck C18
* eluent: Acetonitrile:H₂O (52:48 v/v)
* flowrate: 1 ml/minute
* detector: U.V., 333 nm
* temperature: 35° C.

Physical-Chemical Characteristics of Antibiotic AB-023b

The Antibiotic AB-023b has the appearance of a yellow powder, characterized by:

(a) good solubility in dimethyl-sulfoxide, methanol, ethanol, methanol:water (1:1, v/v) mixture and ethanol:water (1:1, v/v) mixture, insolubility in water, hydrocarbons, acetonitrile, methylene chloride, chloroform;

(b) approximate elemental analysis, as determined on one sample kept under vacuum at 40° C. for two hours, as percent values: carbon: 65.18; hydrogen: 8.87; the product does not contain nitrogen, phosphorus and sulfur;

(c) the molecular weight of Antibiotic AB-023b is of 564 Da, as it can be inferred from its FAB-MS spectrum, showing a peak at m/z=565 Da, corresponding to [MH]⁺ ion, and a peak at m/z=563 Da, corresponding to [M−H]⁻ ion. The operating conditions are as follows: FAB negative ions and positive ions, Xe at 9.5 kV, matrix glycerol, Finning Mat 8424;

(d) the most probable minimal formula of Antibiotic AB-023b results to be: $C_{32}H_{52}O_8$ as deduced from the data from ¹H-N.M.R. and ¹³C-N.M.R. spectroscopy and from mass spectrometry.

Figure 10:
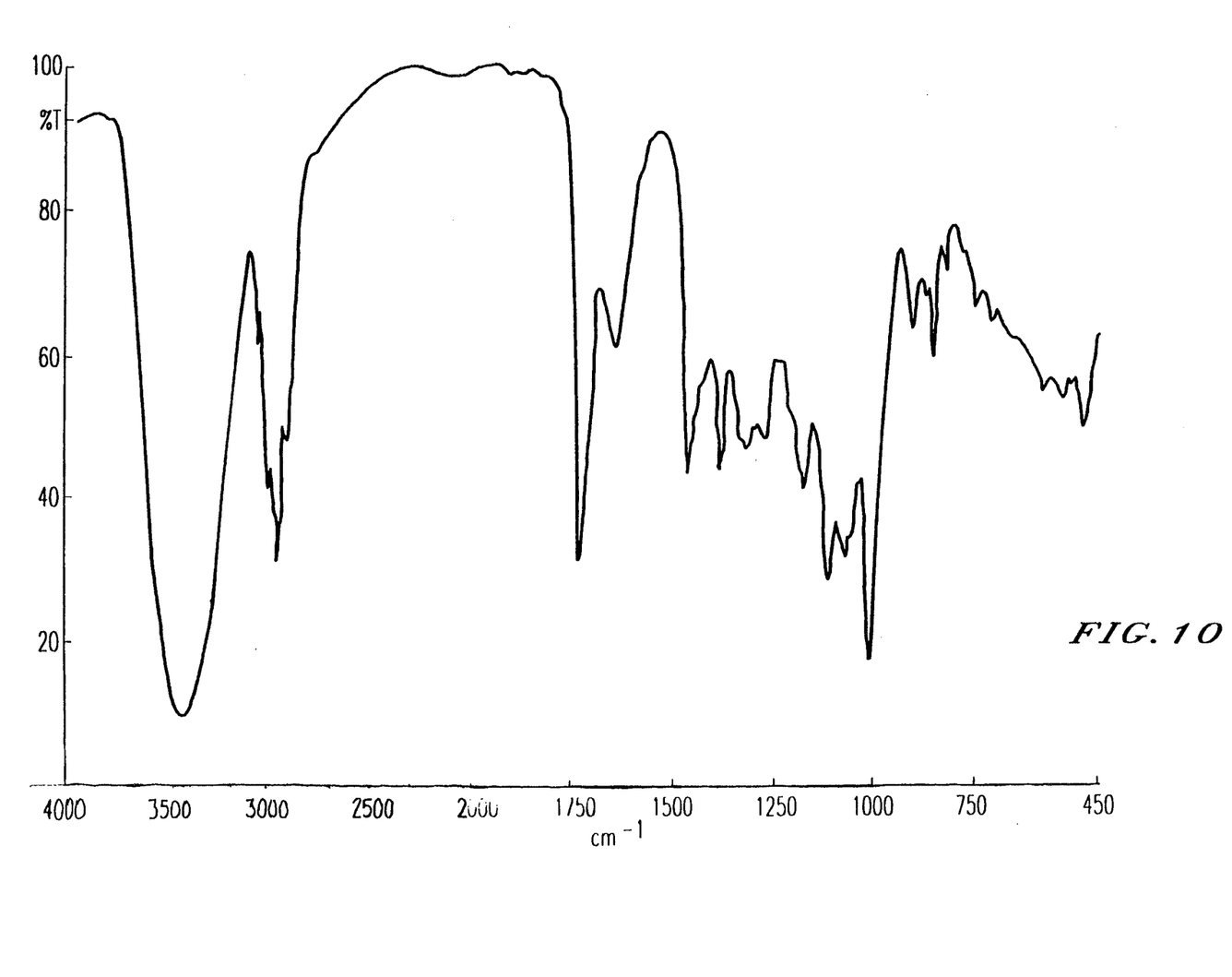
Figure 11:
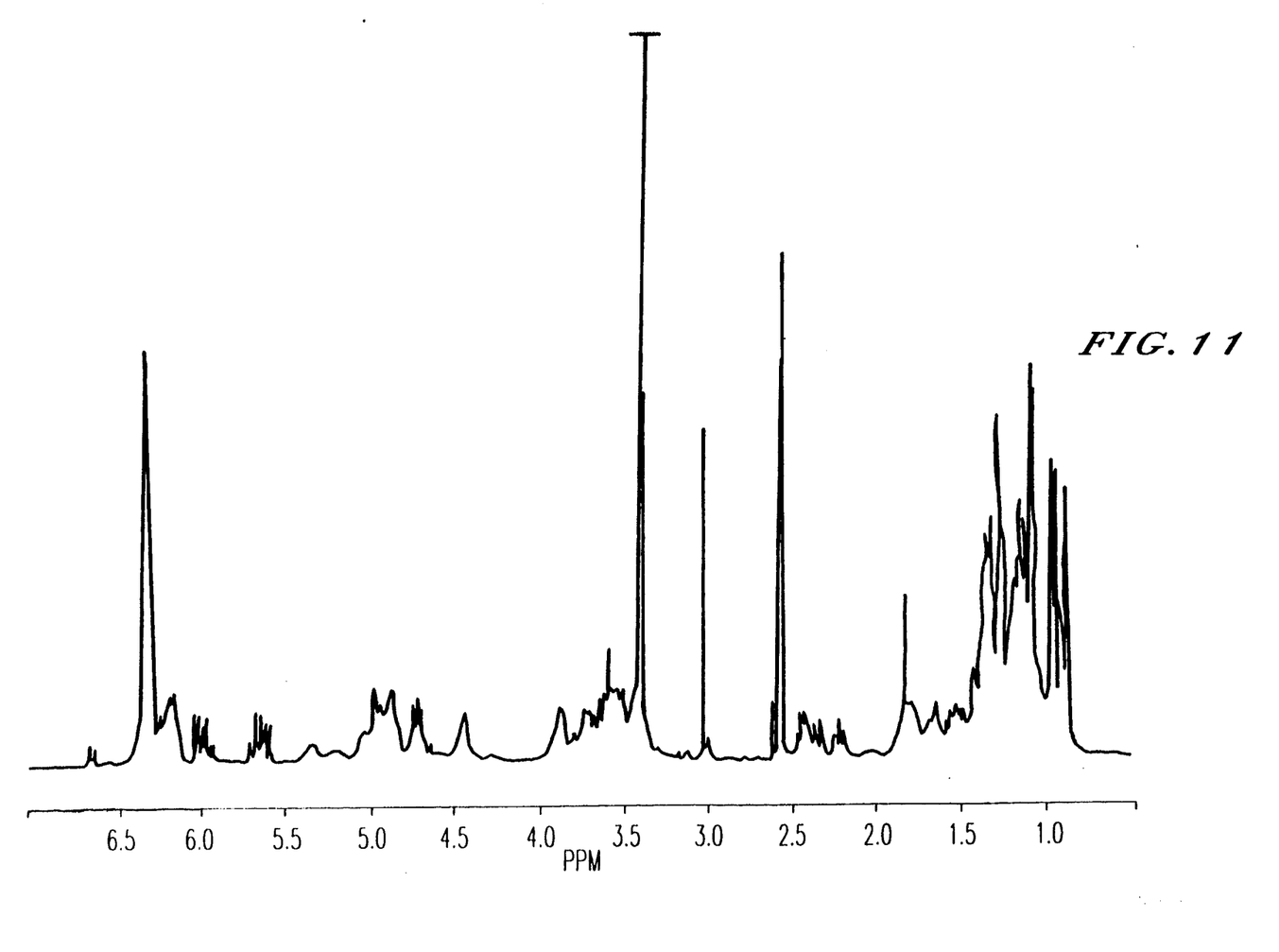
Figure 12:
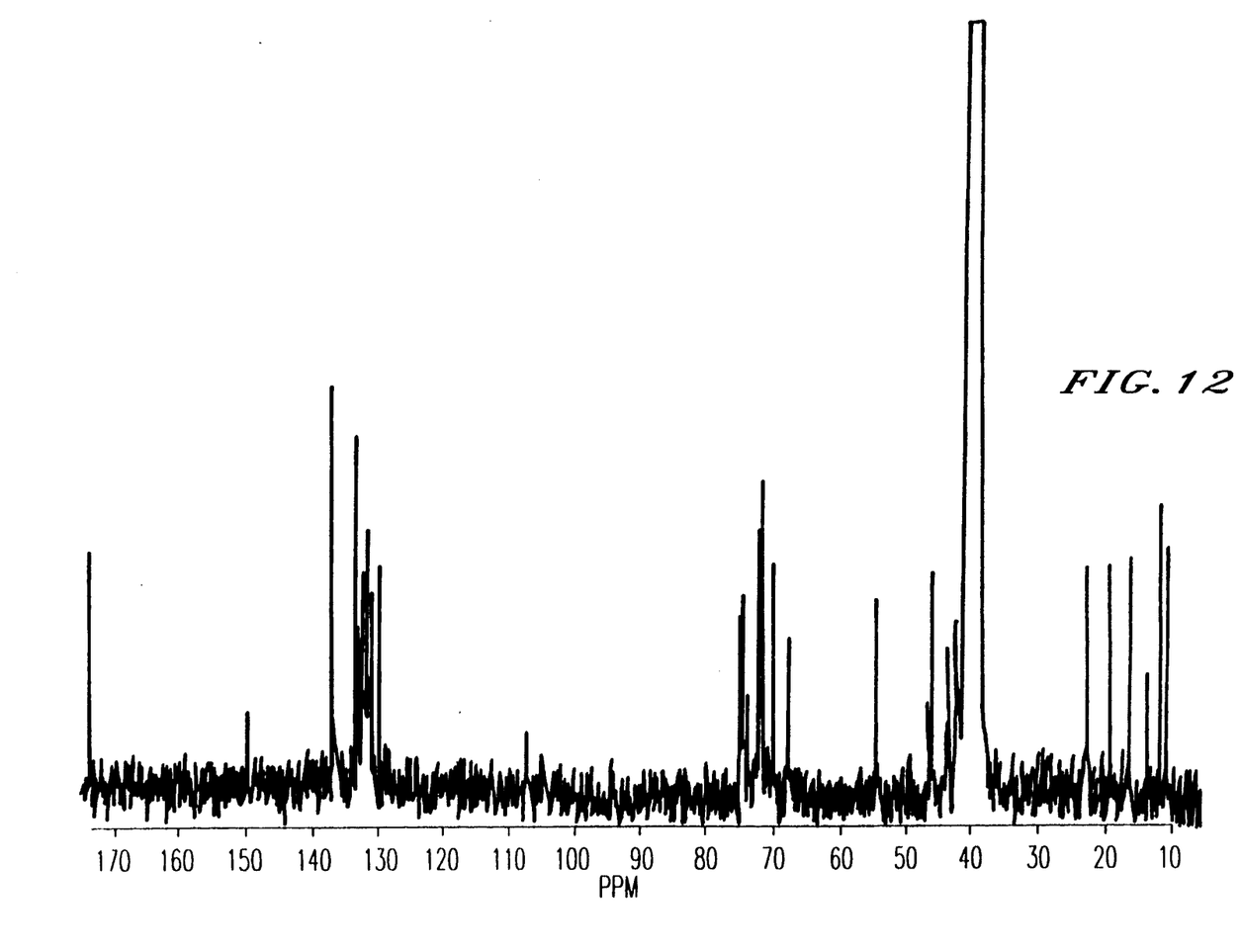

(e) the ultra-violet (U.V.) absorption spectrum is reported in FIG. 5 of the accompanying drawings; it shows absorbance peaks at 303.3 nm (=27536), 317.0 nm (=72192), 332.0 nm (=90562), 348.5 nm (=86534), at a concentration of 0.0070 mg/ml in ethanol;

(f) the infrared (I.R.) absorption spectrum in KBr tablet is reported in FIG. 10 of the accompanying drawings, and shows the following absorption peaks (cm$^{-1}$): 3402, 3014, 2970, 2936, 2879, 2041, 1725, 1636, 1457, 1379, 1311, 1266, 1175, 1109, 1072, 1008, 905, 847, 823, 745, 706, 583, 535, 515, 480;

(e) the N.M.R. spectrum of $^1$H is reported in FIG. 11, and shows signals recorded with a Bruker Spectrometer AM at 300 MHz in hexadeutero-dimethylsulfoxide (DMSOd6); the chemical shifts were indirectly referred to TMS=0.00 ppm (TMS) by using as the internal reference the central peak of hexadeutero-dimethylsulfoxide taken at TMS=2.56 ppm (the signals more largely overlapped were identified by means of bidmensional-N.M.R. techniques);

(ppm): 6.43–6.22 (m, 6H); 6.22–6.10 (m, 2H); 5.97 (dd, 1H); 5.60 (dd, 1H); 5.33 (bs, 1H); 5.03 (bs, 1H); 4.96 (bs, 1H); 4.92 (bs, 1H); 4.85 (m, 1H); 4.70 (m, 1H); 4.42 (m, 1H); 3.94–3.36 (m, 6H); 2.41 (m, 1H); 2.32 (m, 1H); 2.20 (m, 1H); 1.92–1.45 (m, 6H); 1.45–1.09 (m, 8H); 1.25 (d, 3H); 1.07 (d, 3H); 0.95 (d, 3H); 0.88 (t, 3H);

(h) the N.M.R. spectrum of $^{13}$C is reported in FIG. 12 and shows signals recorded with a Bruker Spectrometer AM at 300 MHz in hexadeutero-dimethylsulfoxide (DMSOd6); the chemical shifts were indirectly referred to TMS=0.00 ppm (TMS) by using as the internal reference the central peak of hexadeutero-dimethylsulfoxide taken at TMS=39.50 ppm.

The data relevant to the multiplicity of the signals were obtained by means of DEPT experimental tests at 45°, 90°, and 135°;

(ppm): 173.3 (d); 136.7 (d); 136.7 (d); 133.2 (d); 133.2 (d); 132.7 (d); 132.0 (d); 131.6 (d); 131.3 (d); 130.7 (d); 129.4 (d); 74.8 (d); 74.3 (d); 72.1 (d); 71.6 (d); 71.5 (d); 69.9 (d); 67.5 (d); 54.3 (d); 45.6 (d); 43.1 (t); 4.19 (t); DMSO; DMSO; DMSO; DMSO; 22.7 (t); 22.2 (t); 19.1 (q); 15.6 (q); 11.5 (q); 10.4 (q);

(i) the retention coefficients in thin-layer chromatography with an eluent run of 15 cm on reverse-phase silica slabs RP-18 F 254 (Merck-Schuchardt) and on reverse-phase silica slabs RP-8 F 254 (Merck-Schuchardt), in the following eluent systems are:
* A eluent=water
* B eluent=acetonitrile
* C eluent=methanol
* D eluent=10 mM solution of KH$_2$PO$_4$ in H$_2$O adjusted at pH=3 with H$_3$PO$_4$;

|  | A:B 50:50 (v/v) eluent system | | C:D 70:30 (v/v) eluent system | |
| --- | --- | --- | --- | --- |
| AB-023b | RP-8 | RP-18 | RP-8 | RP-18 |
|  | 0,28 | 0,16 | 0,12 | 0.00 |

Visualization:
(1) fluorescence under UV-light (366 nm)
(2) reactant prepared by dissolving 20 g of (NH$_4$)$_3$MoO$_4$ and 1 g of Ce(SO$_4$)$_2$ in an aqueous solution containing 6% of H$_2$SO$_4$;

(1) the retention time of Antibiotic AB-023b is of approximately 6.76 minutes when analysed by HPLC on a reverse-phase column under the following conditions:
* column: Merck's Lichrosorb RP-18, mm 250×4
* precolumn: Merck C18
* eluent: Acetonitrile:H$_2$O (52:48 v/v)
* flowrate: 1 ml/minute
* detector: U.V., 333 nm
* temperature: 35° C.

Morphology and cultural characteristics of the microorganism Streptomyces sp. NCIMB 40212.

The microorganism Streptomyces sp. NCIMB 40212 was isolated from a soil sample collected at Nairobi (Kenia) and recorded, for internal laboratory use, with the conventional code SD-581.

On Oct. 3rd, 1989, a culture of this microorganism was deposited, in pursuance of the Budapest Covenant, with the National Collection of Industrial Bacteria (c/o The National Collection of Industrial and Marine Bacteria, Ltd., Torrey Research Station,, P.O. Box 31, Abbey Road, Aberdeen AB DG - U.K.), were it was assigned the NCIMB access number 40212.

The morphological characteristics of the microorganism are reported in following Table A (the culture substrates are indicated with their name as reported in International Streptomyces Program).

In Tables B and C, some characteristics concerning the culture of this strain are reported.

TABLE A

| | | | Morphology on several culture substrates | | |
| --- | --- | --- | --- | --- | --- |
| Substrate | ISP (1) | Growth (2) | Base Mycelium | Aerial Mycelium | Soluble Pigment |
| Malt extract | M2 | +++ | raised, light colour | abundant, gray colour | — |
| Dat Heal Agar | M3 | ++ | smooth, yellow colour | scarce, gray colour | — |
| Starch Agar | M4 | +++ | raised, light colour | abundant, gray colour | — |
| Glycerol Asparagine | M5 | +++ | smooth, yellow colour | abundant, gray colour | — |
| Peptone Yeast Extract | M6 | ++ | smooth, yellow colour | abundant, gray colour | — |
| Tyrosine Agar | M7 | ++ | smooth, light colour | scarce, white colour | — |
| Czapek Peptone | | ++ | smooth, light colour | scarce, gray colour | — |
| Dextrose Potato | | +++ | smooth, light colour | abundant, gray colour | — |
| Nutrient Agar | | +++ | smooth, yellow colour | abundant, white colour | light, yellow colour |
| Water Agar | | ++ | smooth, light colour | scarce, gray colour | — |

TABLE B

| Antibiogram (4) | | |
| --- | --- | --- |
| Antibiotic | Dose (g) | Sensibility |
| Nalidixic Acid | 30 | ++ |
| Ampicillin | 10 | — |
| Bacitracin | 10 | ++ |
| Cefaloridin | 30 | — |
| Chloramphenicol | 30 | + |
| Chlorotetracycline | 30 | + |
| Erythromycin | 15 | +++ |
| Fosfomycin | 50 | — |
| Gentamycin | 10 | + |
| Kanamycin | 30 | ++ |
| Lincomycin | 2 | — |

TABLE B-continued

| Antibiotic | Antibiogram (4) Dose (g) | Sensibility |
|---|---|---|
| Neomycin | 30 | + |
| Novobiocin | 30 | +++ |
| Oleandomycin | 15 | +++ |
| Oxytetracycline | 30 | + |
| Penicillin | 10 | − |
| Rifamycin | 30 | ++ |
| Rifampicin | 30 | +++ |
| Streptomycin | 10 | + |
| Tetracycline | 30 | + |
| Tobramycin | 10 | + |
| Vancomycin | 30 | ++ |

TABLE C

| Compound | Auxanogram (3) Growth (2) |
|---|---|
| Adonitol | − |
| L-Arabinose | − |
| Cellobiose | − |
| Galactose | − |
| Glucose | + |
| Glycerol | +++ |
| Inositole | − |
| Lactose | − |
| Maltose | +++ |
| Methyl-D-glucoside | − |
| Melezitose | − |
| N-Acetyl-D-Glucosamine | +++ |
| Raffinose | − |
| Saccharose | − |
| Sorbitol | − |
| Trehalose | − |
| Xylitol | − |
| Xylose | − |
| 2-Keto-D-Gluconate | − |

Remarks:
(1) Code assigned by the International Streptomyces Program.
(2) + = poor;
++ = good;
+++ = abundant.
(3) Performed by using the API systems SA's API:API 200 Kit.
(4) Performed by using the Sensi-Disc (of 5 mm of diameter), marketed by BBL (Becton Dickinson Microbiology Systems).

The analysis by scanning electron microscopy shows that the mycelium of *Streptomyces sp.* NCIMB 40212 tends to form filaments constituted by a plurality of twisted Hyphae and that the spore chains are of recti-flexible type, with smooth spores. These features assign NCIMB 40121 strain to Streptomyces genus.

Like other microorganisms, *Streptomyces sp.* NCIMB 40212 may undergo either natural or artificial variations and/or mutations.

For example, artificial variants or mutants can be obtained by treating the microorganism with chemical mutagenic agents such as, e.g., nitrous acid, nitrosoguanidine, halogenated alkyl-amines and the like, or with such physical agents as X rays, ultraviolet light (U.V.), or high-frequency waves.

Natural variants or mutants can be obtained as well, by isolating and selecting different colonies obtained from *Streptomyces sp.* NCIMB 40212.

All either natural or artificial variants and/or mutants belonging to Streptomyces genus and producing AB-023 Antibiotics are considered as equivalent to microorganism *Streptomyces sp.* NCIMB 40212 and fall within the scope of the instant invention.

Process for Preparing Antibiotics AB-023

The process for preparing the Antibiotics AB-023 consists in cultivating *Streptomyces sp.* NCIMB 40212, or a natural or artificial variant thereof, under controlled aerobic fermentation conditions, in an aqueous nutrient substrate and separating said AB-023 Antibiotics by means of per se known methods.

As the nutrient culture substrates, those substrates can be used, which are customarily used for producing antibiotics; however, some nutrient culture media will be preferred.

Said culture substrates must contain carbon and nitrogen sources which must be assimilable by the microorganisms belonging to Streptomyces genus; they must furthermore contain low concentrations of inorganic salts, and traces of those metals which are necessary for the growth and development of the microorganisms, and for the production of antibiotics. Said metal traces may be already present, as impurities, in the organic nitrogen and carbon sources included in the culture substrates in order to allow the bacterial growth, or, whenever necessary, can be added to said culture substrates.

In general, as the source of assimilable carbon, there can be used carbohydrates, in particular, saccharides, such as, e.g., dextrose, maltose, lactose, or, either alternatively or as a complement, starches and those industrial products which are chemically related to starches, such as, e.g., dextrose or soluble starch, or also polyhydroxy alcohols, such as, e.g., glycerol. Said compounds can be used either as individual compounds, or as combinations thereof, in variable mutual proportions.

The concentration and the type of carbon source contained in the culture substrate depend in general on the type and amount of the other components of the substrate; however, concentrations comprised within the range of from 0.5 to 5% by weight are satisfactory.

As the source of organic nitrogen, there can be used proteinic extracts such as, e.g., yeast extract, meat extract and casein hydrolysate, or meals, such as, e.g., soy bean meal, or industrial products marketed for this purpose, such as, e.g., <<Proflo>>, <<Corn Steep Liquor>> and <<Distillers Solubles>>. These compounds can be used either individually, or as combinations thereof, in variable proportions. Their concentrations in the culture substrate may be comprised within the range of from 0.2 to 6% by weight.

As regards the inorganic salts, there can be used, e.g., such sodium, potassium, magnesium, iron, ammonium and calcium salts, as phosphates, sulfates, chlorides, carbonates and nitrates.

The metals present in trace amounts in the culture substrate can be, e.g., cobalt, iron, manganese, and the like.

Some culture substrates have displayed a capability of stimulating the production of Antibiotics AB-023 by *Streptomyces sp.* NCIMB 40212. Among them, the aqueous formulations, which are used in the following examples of preparation, can be mentioned:

| (Ingredients) | (concentration, g/l) |
|---|---|
| <<A>> Culture Substrate (PM8) | |
| Starch | 20 |
| Glucose | 10 |
| Calcium carbonate | 3 |
| Hydrolysed casein | 2 |
| Proflo | 2 |
| Yeast extract | 2 |
| Meat extract | 2 |
| pH | 7,0 |
| <<B>> Culture Substrate (PGC) | |
| Glycerol | 30 |

-continued

| (Ingredients) | (concentration, g/l) |
|---|---|
| Proflo | 20 |
| CaCO$_3$ | 3 |
| pH | 6.5-7.0 |

The microorganism *Streptomyces sp.* NCIMB 40212 can be cultivated and fermented in order to produce Antibiotics AB-023, at temperatures comprised within the range of from 20° C. to 35° C., preferably of from 25° C. to 30° C.

The pH values can generally be comprised within the range of from about 5 to about 9.

The sterile air blown through the culture substrate is used in general in such amounts, as to maintain in the substrate an oxygen concentration of more than 20% of saturation concentration.

The production of Antibiotics AB-023, during the fermentation, can be monitored by checking the biological activity on broth samples, using the fungal species sensible to the same Antibiotics.

The fermentation is continued for a long enough time, until a substantial antibiotic activity is achieved: time periods comprised within the range of from 24 to 150 hours are generally enough.

Separation and Purification of Antibiotic Complex AB-023 and its Antibiotic AB-023a and Antibiotic AB-023b Components After the cultivation under the above disclosed fermentation conditions, the Antibiotic Complex AB-023 can be separated from the culture broth, and subsequently purified, by means of conventional methods known from fermentation art.

Such methods comprise, e.g., the extraction with solvents, precipitation with non-solvents, ultrafiltration, column chromatography in direct- or reverse-phase mode, chromatography on non-ionic or ionic macroporous resins, and the like.

The antibiotics produced during the fermentation are contained in the myceliar mass.

A preferred method in order to recover the Antibiotic Complex AB-0232 consists in centrifuging off the myceliar mass from the culture broth, submitting the so separated mycelium to an extraction with ethanol or aqueous ethanol, separating the exhausted mycelium from the alcoholic extract by paper filtration, and vacuum-concentrating the extract to dryness, in order to obtain a raw product.

The Antibiotic Complex AB-023 is then isolated from said raw product, by adsorption on non-ionic polystyrene resin, for example, of XAD-4 type (available from Röhm and Haas Co.). The resin is then washed with 2 volumes—as referred to the volume of the resin bed—of water, and then is eluted with 3 volumes—also as referred to the volume of the resin bed—of an eluent system formed by an <<A>> eluent consisting of water, and a <<B>> eluent constituted by methanol-:acetonitrile (50:50, v/v), with a gradient of from 20% to 80% of <<B>> eluent.

The fractions which contain the Antibiotic Complex AB-023, identified by biological tests for activity on Botrytis, are chromatographed by using a column packed with reverse-phase silica of MATREX Silica C18 type (available from Amicon Europe, Lausanne, Switzerland), with an eluent system formed by an <<A>> eluent consisting of water, and a <<B>> eluent constituted by acetonitrile, with a linear gradient of from 20% to 80% of the <<B>> eluent in the <<A>> eluent.

The fractions which contain the Antibiotic Complex AB-023 are combined and concentrated under vacuum, until no acetonitrile is present any longer. From the so-obtained aqueous suspension, the Antibiotic Complex AB-023 precipitates by cooling, as a solid, yellow-coloured substance.

After centrifuging off the aqueous supernatant, and drying the precipitate under the vacuum of the rotary pump, the Antibiotic Complex designated AB-023 is obtained, which is prevailingly constituted by Antibiotics AB-023a and AB-023b, in a mutual ratio of about 1:1.

The individual AB-023a and AB-023b antibiotics can be separated from each other by submitting the Antibiotic Complex AB-023 to a further chromatographic separation, on a reverse-phase silica column of MATREX Silica C18 tyoe (available from Amicon Europe, Lausanne, Switzerland), with an eluent system formed by an <<A>> eluent consisting of water, and a <<B>> eluent constituted by acetonitrile, with a gradient of from 20% to 80% of the <<B>> eluent in the <<A>> eluent.

Biological Activity

The Antibiotic Complex AB-023 and its Antibiotic AB-023a and Antibiotic AB-023b components display an antifungal activity, against the pathogen fungi which infest the cereal crops, fruit trees and horticultural crops, as well as against pathogen fungi which attack man.

The antifungal activities in vitro of antibiotics AB-023 were determined by the methods disclosed hereinafter.

Test for <<In Vitro>> Fungicidal Activity

The antimicrobial activity of the Antibiotics AB-023 is determined by means of the usual methods, by adding increasing concentrations of the antibiotic to an agarised substrate capable od supporting the growth of the sensible microbial species. For phytopathogen fungi, the minimum concentration—expressed as ppm—was determined of Antibiotics AB-023 which, under these conditions, completely inhibits the growth (Minimal Inhibitory Concentration, MIB). In Table D, the data of biological activity are reported, which were obtained in vivo by means of the methods described hereinabove.

TABLE D

| TEST FUNGUS | Minimal Inhibitory Concentration, ppm |
|---|---|
| *Botrytis cinerea* | 5 |
| *Helminthosporium teres* | 10 |
| *Fusarium roseum* | 10 |
| *Fusarium moniliforme* | 25 |
| *Rhizoctonia solani* | 10 |
| *Colletotricum coffeanum* | 10 |
| *Piricularia orizae* | 10 |
| *Pithium ultimum* | 100 |
| *Candida albicans* | 10 |
| *Sarcina lutea* | 100 |

Very similar results of antifungal activity are obtained by using the individual components Antibiotic AB-023a and Antibiotic AB-023b.

For the purposes of their practical use, both in agriculture and in other use sectors, the antibiotics according to the present invention are advantageously used as suitable compositions.

These compositions contain, besides the antibiotic of the invention as their active principle, inert carriers, which may be either solid substances (such as, e.g., China clay, silica, talc, actapulgite, diatomaceous earth, and so forth) or liquid substances (e.g., organic solvents, vegetable or mineal oils, water, and mixtures thereof), and, possibly, such other additives as normally used in the formulation field, such as surface active agents, suspending agents, dispersants and wetting agents.

For particular formulation requirements, or in order to expand the activity range of the compositions, to said compositions, as disclosed hereinabove, further active ingredients may be added, such as, e.g., insecticides, herbicides and fungicides.

The application doses may vary depending on several factors, such as the type and level of infestation, the type of composition used, weather and environmental factors.

For practical uses in agriculture, doses of AB-023 antibiotics comprised within the range of from 10 to 500 g/hectare yield satisfactory results.

Some examples are given now for the purpose of illustrating the invention without limiting it.

EXAMPLE 1

A culture of Streptomyces sp. NCIMB 40212 grown on a slant agar-<<A>> substrate (PM8) culture, was re-suspended in 5 ml of sterile distilled water. Such a suspension was inoculated into an Erlenmeyer flask containing 100 ml of <<A>> substrate (PM8). The Erlenmeyer flask was then kept shaked at 180 rpm, at 28° C., for 55 hours. The resulting culture was used to inoculate a matras containing 1 liter of <<A>> substrate (PM8), which was subsequently kept shaked at 150 rpm, at 28° C. for 40 hours. With the resulting culture, a fermentor with a rated volume of 40 liters, containing 28 liters of <<B>> substrate (PGC), was then inoculated. The fermentation was sustained for 24 hours, with the temperature being kept at 28° C. and the concentration of dissolved oxygen being kept higher than 20% of saturation concentration.

EXAMPLE 2

A culture of Streptomyces sp. NCIMB 40212 grown on a slant agar-<<A>> substrate (PM8) culture, was re-suspended in 6 ml of sterile distilled water. Such a suspension was inoculated into three Erlenmeyer flasks, each of which contained 100 ml of <<A>> substrate (PM8). The Erlenmeyer flasks were then kept shaked at 180 rpm, at 28° C., for 48 hours. The resulting culture was used to inoculate 50 Erlenmeyer flasks, each of which contained 100 ml of <<B>> substrate (PGC), with an inoculum of 5% by volume. The Erlenmeyer flasks were kept stirred at 180 rpm, at 28° C. for 72 hours. The so obtained broth was then collected and separated from the mycelium by centrifugation at 6,000 rpm for 20 minutes.

Isolation of Antibiotic Complex AB-023

10 liters of fermentation broth were separated from the mycelium, by centrifugation. The separated mycelium was extracted with aqueous ethanol, then the ethanolic exctract of mycelium was vacuum-concentrated down to a small volume, and was percolated on a nonionic polystyrene column, of XAD-4 type (available from Röhm and Haas Co.). The resin was washed with 2 volumes, as referred to the same resin bed volume, of water, and was then eluted with 3 volumes, also referred to the same resin bed volume, of an eluent system formed by an <<A>> eluent consisting of water, and a <<B>> eluent consisting of methanol:acetonitrile (50:50, v/v), with a gradient of from 20% to 80% of the <<B>> eluent in the <<A>> eluent. The fractions containing the Antibiotic Complex AB-023 were combined and concentrated to dryness, in order to yield a raw product.

Said raw product was dissolved again with 50 ml of a water:acetonitrile mixture (20:80, v/v), with which a reverse-phase silica column was conditioned (MATREX Silica C-18, Amicon Europe, Lausanne, Switzerland) (diameter of the column 33 mm, height of silica bed 30 cm). The Antibiotic Complex AB-023 was then eluted from the above said chromatographic column by using an eluent system formed by acetonitrile and water, with a gradient comprised within the range of from 20% to 80% of acetonitrile, with a volume of 300 ml of eluent being used each time. The fractions containing the Antibiotic Complex AB-023, identified by means of the biological test on Botrytis, were combined and vacuum-concentrated, until no acetonitrile was detected any longer.

From the resulting aqueous suspension the Antibiotic Complex designated <<AB-023>> precipitated on cooling, as a yellow-coloured solid. After centrifugation and drying, 300 mg of Antibiotic Complex AB-023, prevailingly formed by Antibiotic AB-023a and Antibiotic AB-032b, in an approximate mutual ratio of 1:1, was obtained.

Isolation of Antibiotic AB-023a and Antibiotic AB-023b

Antibiotic AB-023a and Antibiotic AB-023b were isolated from AB-023 complex by repeating a chromatography on reverse-phase silica column (MATREX Silica C-18, Amicon Europe, Lausanne, Switzerland) (diameter of the column 22 mm, height of silica bed 50 cm), by using an eluent system formed by an <<A>> eluent consisting of water, and a <<B>> eluent consisting of acetonitrile, with a linear gradient comprised within the range of from 20% to 80% of the <<B>> eluent in the <<A>> eluent.

Some fractions which contained pure Antibiotic AB-023a, and some fractions which contained pure Antibiotic AB-023b were obtained, besides some fractions which contained the mixture of both, as AB-023 Complex. By concentrating to dryness, under vacuum, the fractions which contained Antibiotic AB-023a and Antibiotic AB-023b in pure form, 50 mg of Antibiotic AB-023a and 15 mg of Antibiotic AB-023b were obtained as yellow-coloured solid substances.

The physical-chemical of the product are reported above in the instant disclosure.

We claim:

1. A method for treating fungal infestation, comprising applying to, the fungus an effective amount of a compound selected from the group consisting of Antibiotic Complex AB-023, Antibiotic AB-023a and Antibiotic AB-023b.

* * * * *